(12) United States Patent
Miraki (10) Patent No.: US 10,687,802 B2
(45) Date of Patent: Jun. 23, 2020

(54) SYSTEMS AND METHOD FOR DEPLOYING SURGICAL SUTURE

(71) Applicant: Edwards Lifesciences Corporation, Irvine, CA (US)

(72) Inventor: Manouchehr A. Miraki, Laguna Hills, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 113 days.

(21) Appl. No.: 15/445,574

(22) Filed: Feb. 28, 2017

(65) Prior Publication Data

US 2017/0252035 A1    Sep. 7, 2017

Related U.S. Application Data

(60) Provisional application No. 62/302,540, filed on Mar. 2, 2016.

(51) Int. Cl.
*A61B 17/06* (2006.01)
*A61B 17/04* (2006.01)
*A61B 17/00* (2006.01)

(52) U.S. Cl.
CPC .......... *A61B 17/06* (2013.01); *A61B 17/0483* (2013.01); *A61B 17/06109* (2013.01);
(Continued)

(58) Field of Classification Search
CPC ............... A61B 17/0483; A61B 17/06; A61B 17/06109; A61B 17/06123;
(Continued)

(56) References Cited

U.S. PATENT DOCUMENTS

| 3,840,017 A | * 10/1974 | Violante ............... A61B 17/04 606/146 |
| 5,350,385 A | 9/1994 | Christy |

(Continued)

FOREIGN PATENT DOCUMENTS

| EP | 0755655 A2 | 1/1997 |
| EP | 0755656 A2 | 1/1997 |

(Continued)

OTHER PUBLICATIONS

Int'l. Search Report for PCT/US2017/020484, dated Jun. 13, 2017.

*Primary Examiner* — Kathleen S Holwerda
*Assistant Examiner* — Brooke Labranche
(74) *Attorney, Agent, or Firm* — Chang & Hale (57) ABSTRACT

A device for suturing an incision in an artery has a handle, a supply of suture stored on spindle housed in the handle, a tube extending from the handle having a lumen through which suture extends, and a curved needle at a distal end of the handle, the curved needle having an opening through which a free end of the suture extends. A method for suturing an incision in an artery includes creating sequential openings in first and second flaps of the incision, with loops of suture extending through openings in one flap, with a free end of suture extending through the second flap being pulled through the loops and secured to another free end of suture extending through the first flap, to close the incision.

21 Claims, 7 Drawing Sheets

(52) U.S. Cl.
CPC .............. *A61B 17/06123* (2013.01); *A61B 2017/0042* (2013.01); *A61B 2017/00424* (2013.01); *A61B 2017/00438* (2013.01); *A61B 2017/00663* (2013.01); *A61B 2017/061* (2013.01); *A61B 2017/0608* (2013.01); *A61B 2017/06052* (2013.01); *A61B 2017/06076* (2013.01)

(58) Field of Classification Search
CPC .. A61B 2017/0042; A61B 2017/00424; A61B 2017/00438; A61B 2017/00663; A61B 2017/06052; A61B 2017/06076; A61B 2017/0608; A61B 2017/061
See application file for complete search history.

(56) References Cited

U.S. PATENT DOCUMENTS

| | | | |
|---|---|---|---|
| 5,503,634 | A | 4/1996 | Christy |
| 5,984,933 | A | 11/1999 | Yoon |
| 6,004,330 | A * | 12/1999 | Middleman ............ A61B 10/02 606/127 |
| 6,221,085 | B1 | 4/2001 | Djurovic |
| 6,626,930 | B1 | 9/2003 | Allen et al. |
| 7,049,244 | B2 | 5/2006 | Becker et al. |
| 7,083,628 | B2 | 8/2006 | Bachman |
| 7,381,210 | B2 | 6/2008 | Zarbatany et al. |
| 7,842,046 | B1 | 11/2010 | Nakao |
| 9,017,347 | B2 | 4/2015 | Oba et al. |
| 9,498,202 | B2 | 11/2016 | Jafari et al. |
| 2003/0204195 | A1* | 10/2003 | Keane ................ A61B 17/0401 606/146 |
| 2004/0204724 | A1 | 10/2004 | Kissel et al. |
| 2005/0251209 | A1 | 11/2005 | Saadat et al. |
| 2006/0089571 | A1 | 4/2006 | Gertner |
| 2006/0265042 | A1 | 11/2006 | Catanese et al. |
| 2006/0276871 | A1 | 12/2006 | Lamson et al. |
| 2007/0005079 | A1 | 1/2007 | Zarbatany et al. |
| 2007/0049970 | A1 | 3/2007 | Belef et al. |
| 2008/0154286 | A1 | 6/2008 | Abbott et al. |
| 2011/0288564 | A1 | 11/2011 | Frings et al. |
| 2012/0022560 | A1* | 1/2012 | Ferreira ............ A61B 17/0469 606/145 |
| 2012/0035654 | A1* | 2/2012 | Belson .................. A61B 90/03 606/232 |
| 2012/0053599 | A1 | 3/2012 | Shikhman et al. |
| 2012/0165865 | A1 | 6/2012 | Fujisaki et al. |
| 2012/0209298 | A1* | 8/2012 | McClurg ............ A61B 17/0469 606/144 |
| 2013/0165953 | A1 | 6/2013 | Oba et al. |
| 2013/0165954 | A1 | 6/2013 | Dreyfuss et al. |
| 2016/0183937 | A1 | 6/2016 | Miraki et al. |

FOREIGN PATENT DOCUMENTS

| | | |
|---|---|---|
| EP | 1484023 A1 | 12/2004 |
| EP | 2455001 A2 | 5/2012 |
| EP | 2462876 A2 | 6/2012 |
| WO | 0128455 A1 | 4/2001 |

\* cited by examiner

SYSTEMS AND METHOD FOR DEPLOYING SURGICAL SUTURE

RELATED APPLICATION

This application claims priority to U.S. Provisional Application No. 62/302,540, filed Mar. 2, 2016, the entire disclosure of which is incorporated by reference herewith.

FIELD OF THE INVENTION

The present invention relates to surgical suturing and, in particular, to an apparatus and method for rapidly deploying surgical suture to close an incision in an artery.

BACKGROUND

Sutures are frequently used with a needle driver in surgical procedures to close an incision in an artery, such as an aorototomy as part of heart surgery. Different suture types and patterns may be used. Examples include purse string sutures, mattress sutures, running sutures, and others known in the art.

In an aorototomy, for example, mattress or running sutures are commonly used to close the incision. As one example, a mattress suture may be employed to pull the opening together, then running sutures used to seal it. Alternatively, a double running suture may be used as a precaution in order to minimize the risk of suture breakage and leakage from the incision site. To finish the suturing, the two free ends of each suture are often tied together in a knot, in order to secure the suture in place.

The suturing process can be tedious and time consuming. Consequently, an apparatus and/or method that is both accurate and time-efficient would be beneficial. The present invention relates to a surgical instrument and method for applying and tying running and mattress sutures to close an incision in an artery, such as an aorototomy during heart valve surgery.

BRIEF SUMMARY OF THE INVENTION

A system for closing an incision in an artery has a handle with a proximal end, a distal end, and an interior space. A supply of suture is stored in the interior space of the handle. A tube that has a lumen extends from a distal end of the handle. A curved needle extends from a distal end of the tube, with suture extending from the interior space of the handle, through the lumen of the tube, and extending out of an opening in the needle.

The system may include optional features as follows, each of which may be employed independently of one another, or in combination with one or more of each other. The interior space of the handle may house a spindle that has a supply of suture stored on the spindle. The interior space may thus include a housing in which suture is stored.

The tube may optionally be a hypotube. In one embodiment, the handle comprises first and second finger holders for manipulating the needle. The first and second finger holders may be rings that are spaced distally from a housing in which a supply of suture is stored. Alternatively, the handle may be a pistol grip. In another embodiment, the handle includes a generally tubular portion for gripping with a hand. The longitudinal axis of the handle may align with the longitudinal axis of the tube. The handle may include a thumb placement area, which may optionally be aligned with a tip of the needle Embodiments of the present invention may include a removable cap over the interior space of the handle. The needle may optionally be helical or, in another embodiment, may be semi-circular or otherwise curved as suitable for the portion of the anatomy to be sutured. The needle may optionally have a beveled tip. In one embodiment, the needle includes a distal portion that extends in the direction of a longitudinal axis of the handle, and a proximal curved portion. In a further optional feature, at least a portion of the needle may be reinforced, such as by a sheath or other reinforcing means.

A method of closing an incision in an artery having a first and a second flap using a device having a curved needle and a supply of suture is also disclosed. The suture may extend from the supply of suture through an opening in the curved needle. The method includes the step of driving a curved needle from which suture extends through a first flap at a first entry point. The needle is rotated in a first rotational direction to drive the needle through the second flap. A first free end of the suture is grasped or secured. The needle is then rotated in a direction opposite to the first rotational direction to remove the needle from the first and second flaps. The needle is moved to a second entry point on the first flap, and is driven through the first flap at the second entry point. The needle is rotated in the first rotational direction to drive the needle through the second flap. A loop of suture extending through the second flap is created. The needle is rotated in a direction opposite to the first rotational direction to remove the needle from the first and second flaps. A second free end of suture extends through the first flap. The first free end of suture is inserted through the loop of suture. The first and second ends of suture are pulled together to close the incision, and the first and second ends are secured.

The method may optionally include other features and steps, each of which may be employed independently of one another, or in combination with one or more of each other. The method may further include creating a plurality of openings in the first and second flaps through sequentially rotating and repositioning the needle. Multiple suture loops may be created, each loop extending through a corresponding opening in the second flap. The first and second ends of suture may be knotted together, or may be clipped together or secured by other means.

The method may further include supplying suture to an opening in the needle from a spool of suture. In one embodiment, a spool is first inserted into a housing in the device, and then a removable cover is secured on the housing.

The method may include creating a plurality of loops of suture through a corresponding plurality of openings in the second flap. A first free end of suture may be extended through the loops. A plurality of suture bridges may be created to extend across openings in the first flap. A second free end of suture may extend from a proximal end of the first flap. The first and second free ends may then be pulled tight to close an incision in the artery.

The method may optionally be performed with a device that has a handle, a supply of suture stored on spindle housed in the handle, a tube extending from the handle having a lumen through which suture extends, and a curved needle at a distal end of the handle. The curved needle having an opening through which a free end of the suture extends.

Again, the inventive concept includes variations, and the optional features noted above may be incorporated into specific embodiments of the invention, either alone or in various combinations as appropriate.

A further understanding of the nature and advantages of the invention will become apparent by reference to the remaining portions of the specification and drawings.

DETAILED DESCRIPTION

Described herein are systems and methods for closing an aorototomy during heart valve surgery. The device and method may also be used on other arteries and/or blood vessels and in other areas of the body requiring suturing, and are not limited to closing arototomies.

FIGS. 1-3b illustrate a device 10 having a spool assembly within the interior of a housing. Suture 12 is wound around the spool 14, the rear of which 14' (FIG. 3B) includes a locking key for engagement with an engaging portion of a suture spool cavity 15. A significant amount of suture, such as 20-25 feet in one non-limiting example, may be wound about the spool 14. The spool is secured within device 10 in a housing 16 (FIGS. 3A & 3B) in the handle of the device 10 to protect the supply of suture. The device includes a removable cap 18 to provide access to the spool when required, and to otherwise protect the spool and to ensure the spool remains within the assembly. The cap 18 may be made with any of a variety of materials, including metals, plastics and composites, for example. The cap may be secured by a variety of means, such as screws 20a and b, snaps, or other methods for removably attaching a cap known in the art.

A portion of the device 10 grasped by the user includes finger openings 22a and 22b. Typically, the user will put their thumb in one of the openings and a forefinger in the other, although different combinations of fingers may be used. The finger openings 22a and 22b permit convenient maneuvering of the device. The finger openings in the device of FIG. 1 may be similar to finger openings in a pair of forceps, for example.

Figures 1, 2:
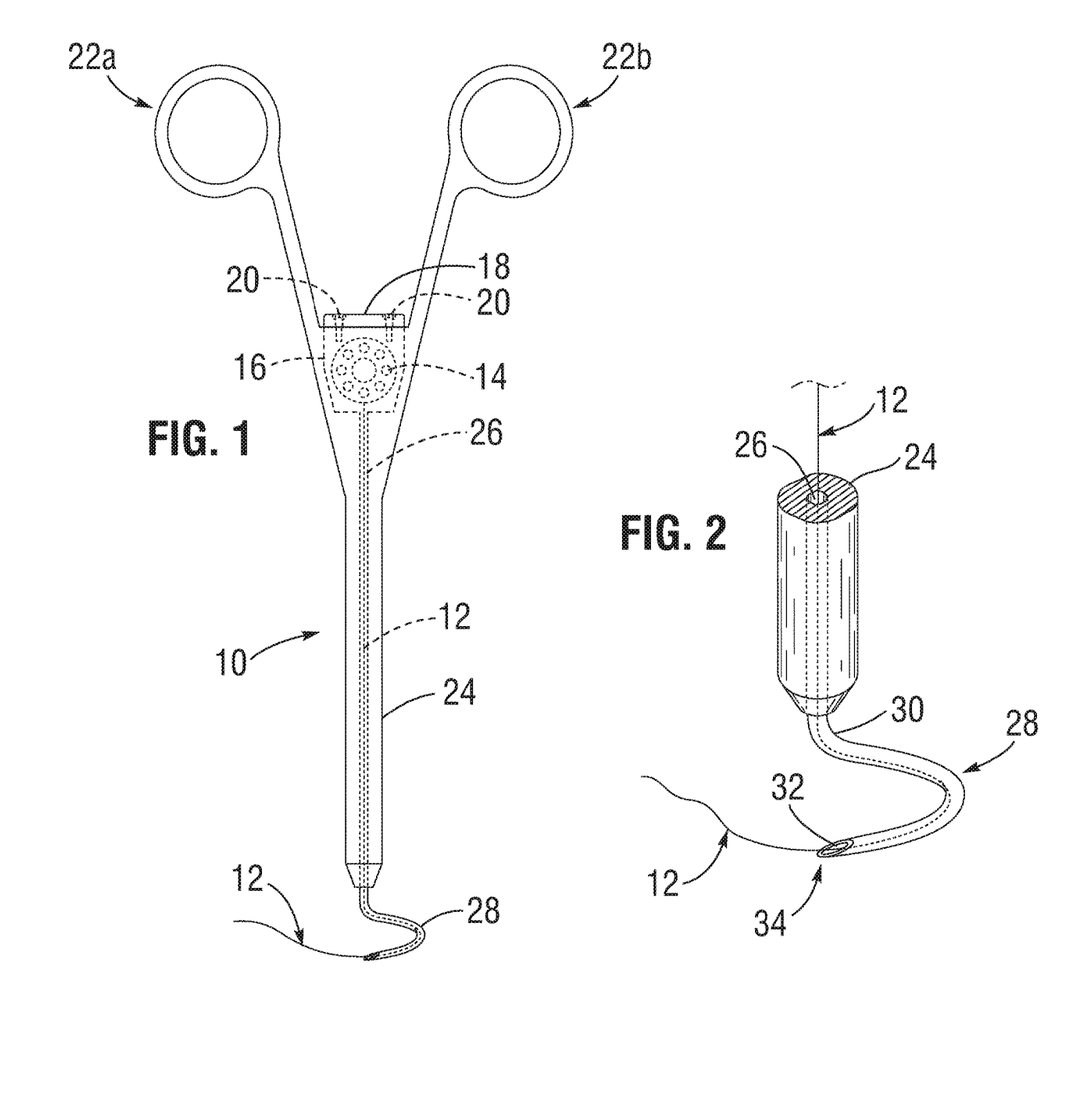
FIG. 1 illustrates a first embodiment of a suture device according to the present invention.
FIG. 2 is a close-up view of the distal needle portion of the embodiment of FIG. 1.
Figure 3A:
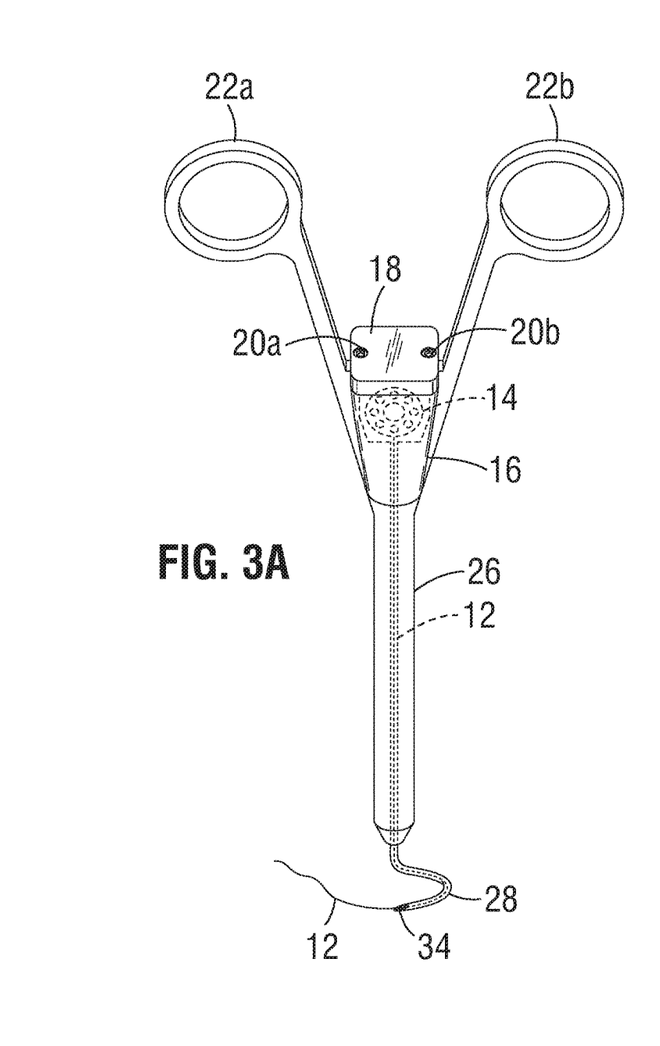
FIG. 3A provides an additional view of the embodiment of FIG. 1, illustrating in particular a removable end cap.
Figure 3B:
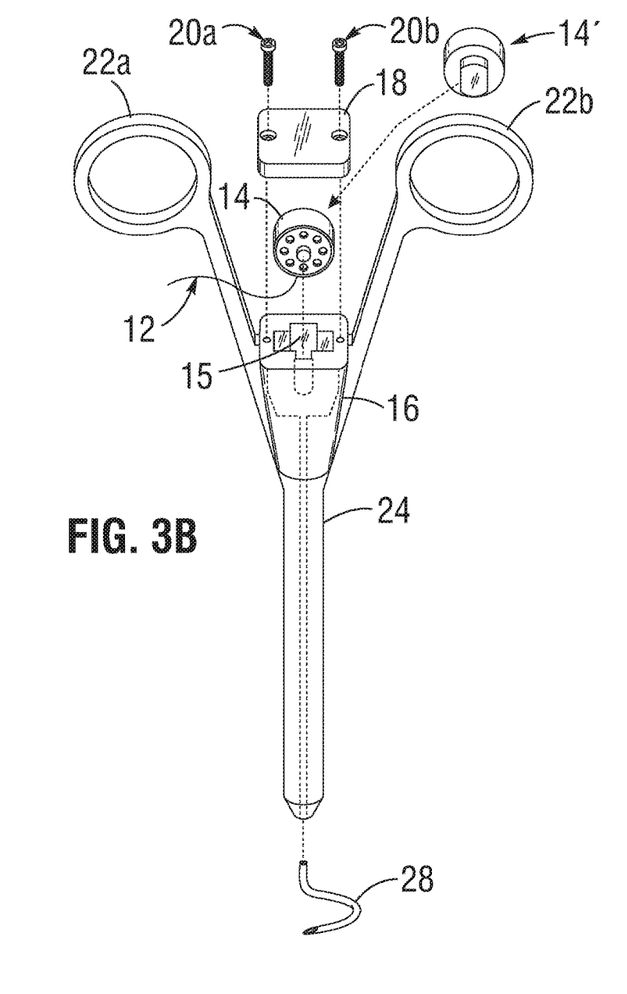
FIG. 3B is an exploded view of components of the embodiment of FIG. 1.

A tube 24 extends towards a distal end of the device. The tube 24 includes a shaft 26 through which suture 12 may extend. Referring particularly to FIG. 2, a curved bevel tip needle 28 extends from the distal end of the tube 24. The needle 28 is, in one non-limiting embodiment, approximately a semi-circle in shape. The needle is bent at bend 30 approximately 90 degrees relative to the finger holder. The needle 28 includes a shaft 26 (FIG. 2) having an opening 32 at a pointed end of the needle 34 through which a free end of suture 12 exits. Typically, the needle 28 is bonded to the tube shaft by methods known in the art, such as laser welding or adhesive. Alternatively, the needle 28 may be a unitary extension of the tube.

To pull the suture from the suture spool 14 through the shaft of the tube and out the end of the bevel tip needle 28, a suture snare may be fed through the shafts of the needle and the tube to grasp the suture and pull it through to the opening 32 of the bevel tip needle 28.

More generally, to assemble one embodiment of a suturing device, the suture 12 is wound onto the spool 14, which is then placed inside the housing 16. The tube shaft 24 extends from the handle portion of the assembly. The tube shaft 24 may be integral to the handle, or may be a separate component that is secured to the handle with welding or another bonding method known in the art, such as adhesive. A snare wire is inserted into the shaft. The end of the suture is loaded onto the snare and is pulled inside the tube shaft 26 until a free end of the suture 12 extends out of the opening in the needle. A cap 18 is placed over the housing, and is secured in place with, for example, screws 20a and 20b or other securing means.

Figure 4:
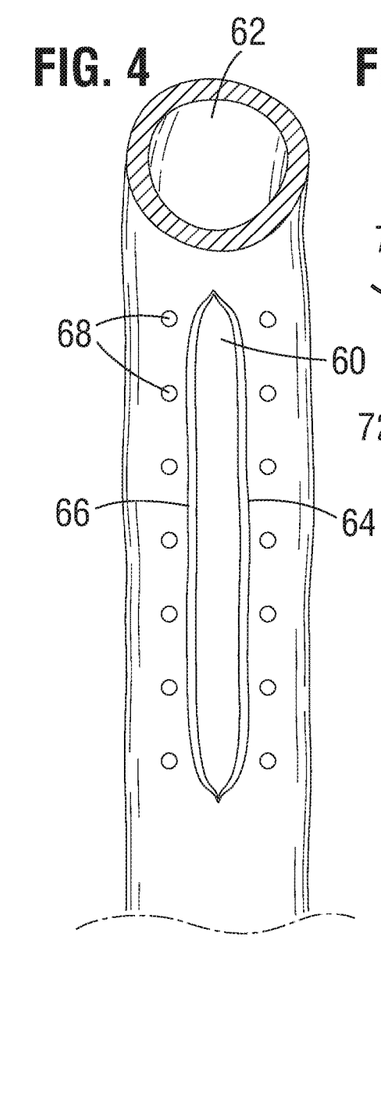
FIG. 4 illustrates an artery and an embodiment of a pattern of openings in the artery made by a device according to the present invention (the suture is not shown for clarity)

As illustrated in FIGS. 4-7, in one method of using a device according to the present invention, an arototomy 60 is cut in the aorta 62 to a desired length. The incision creates a first flap 64 and a second flap 66. Starting from one end of the first flap 64, the needle is driven clockwise through the flap, dragging the suture along with the needle. FIG. 4 illustrates a pattern of openings such as 68 in the flaps that devices according to the present method may be used to create, with suture removed in FIG. 4 for clarity of illustration. The openings 68 include all of the openings along the first and second flaps in FIG. 4. The openings 68 include all of the openings along the first and second flaps in FIG. 4.

Figure 5:
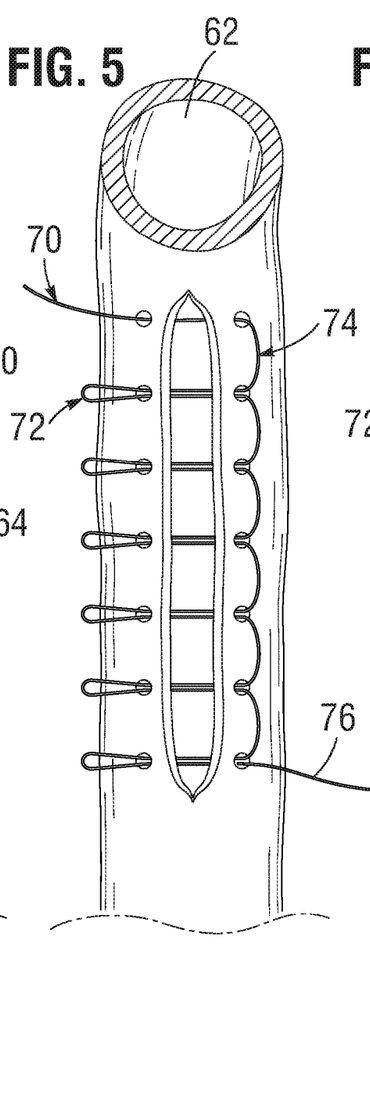
FIG. 5 illustrates the automatic suturing of the artery as the openings of FIG. 4 are being made.

FIG. 5 illustrates the suture that is pulled through the openings 68 as the openings are formed to create a suture pattern. After having pierced the first flap 64, and as the needle continues to be driven clockwise, the needle pierces and extends through the second flap 66. The surgeon then grabs a first free end 70 of the suture, either by hand or with a surgical instrument, and pulls the suture to a desired length. The free end 70 of the suture may then be temporarily secured with forceps, for example, or by other means.

The needle is then rotated in the opposite, counterclockwise direction to remove the needle from the two flaps. The surgeon then moves to a new location spaced a desired distance from the initial needle entry point, and repeats the procedure. This creates a loop 72 on the suture beyond the second flap 66. The loop 72 may be held when necessary by hand or with a surgical instrument. The procedure is continued until the entire arototomy 60 is sutured, creating multiple spaced loops such as 72 extending through the second flap and multiple bridges such as 74 along the first flap. The end of the suture is cut to a desired length to create a second free end 76 extending through an opening of the first flap. The device is then removed from the incision.

Figures 6, 7:
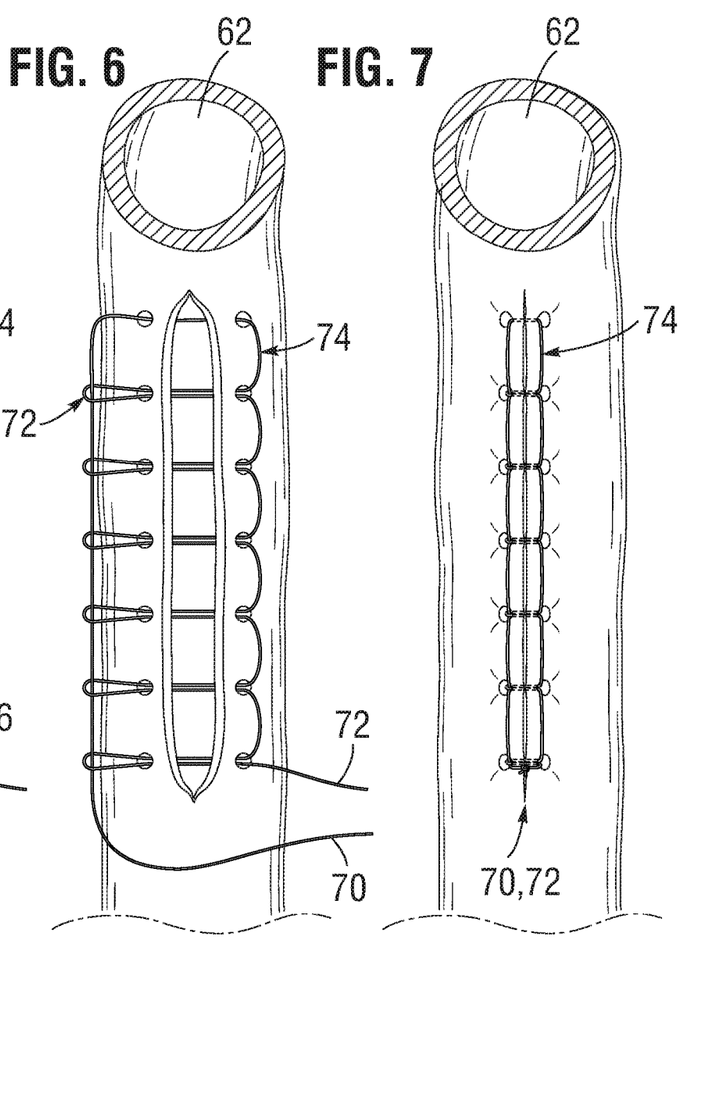
FIG. 6 illustrates a method of interconnecting suture loops to close the opening in the artery.
FIG. 7 illustrates the artery after the incision has been closed.

To complete the procedure, the first free end 70 of the suture is threaded through the suture loops 72, typically with forceps. The two free ends 70 and 76 of the sutures are brought together and secured, such as by knotting. The incision in the aorta is then closed, as in FIG. 7. Alternatively, the suture ends may be secured together with clips, or with other means known in the art. Surplus suture may be trimmed.

Figure 8:
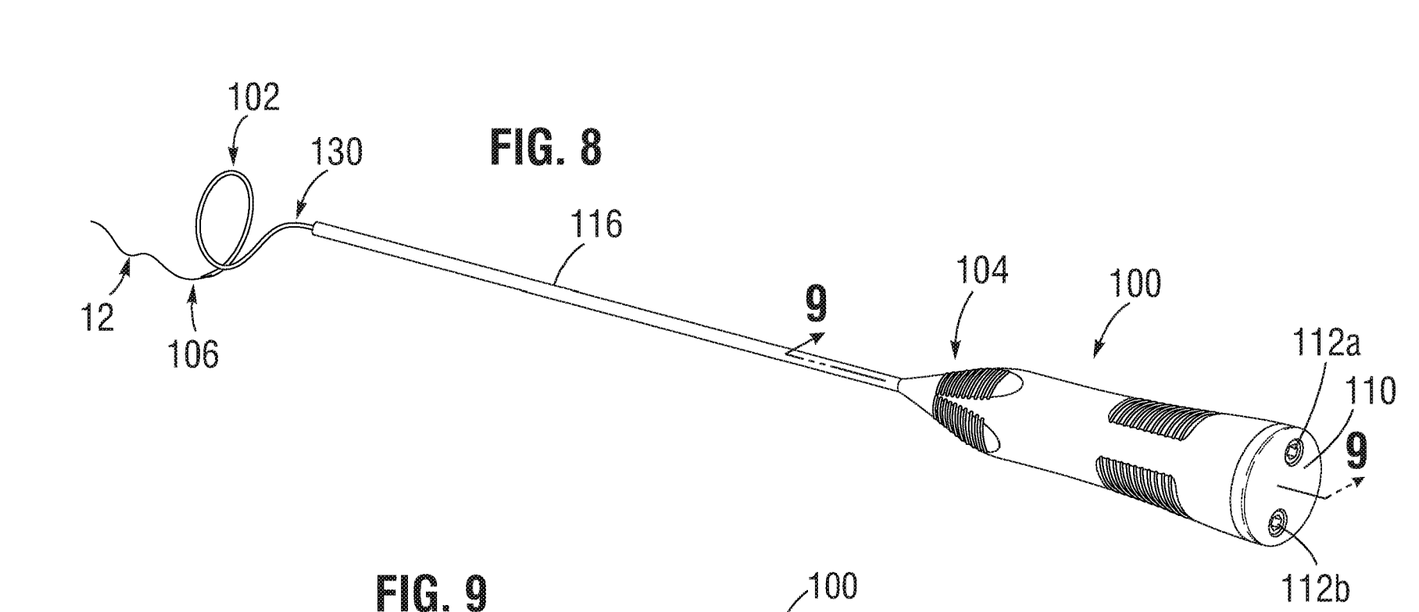
FIGS. 8-10 illustrate an alternative embodiment of a device according to the present invention.
Figure 9:
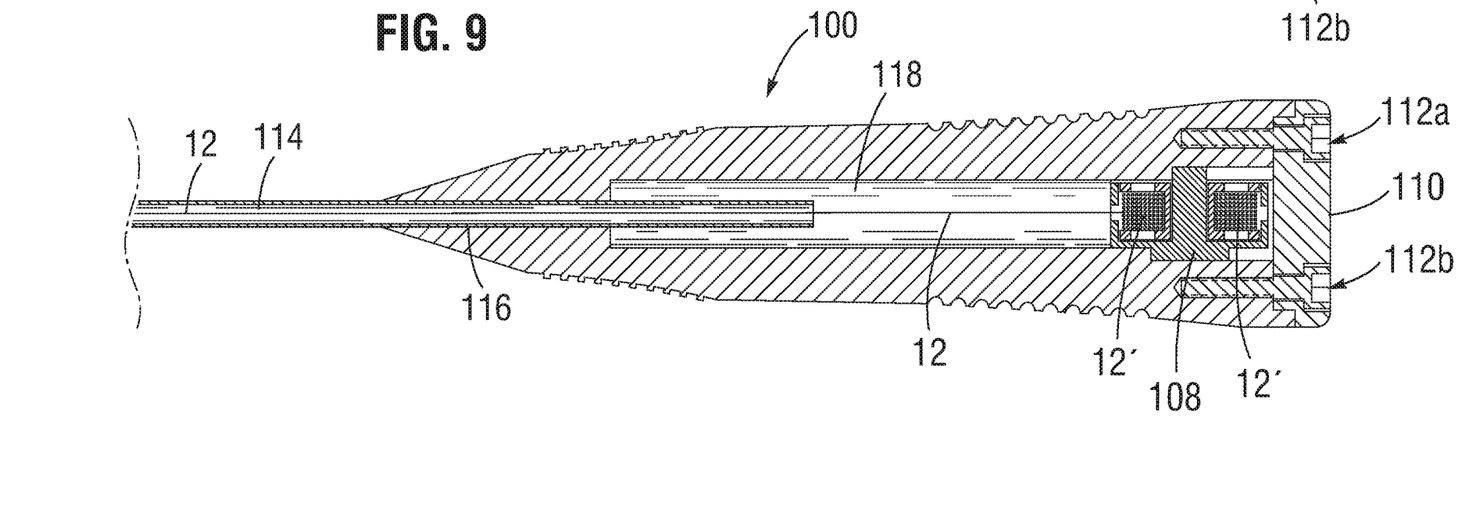
Figure 10:
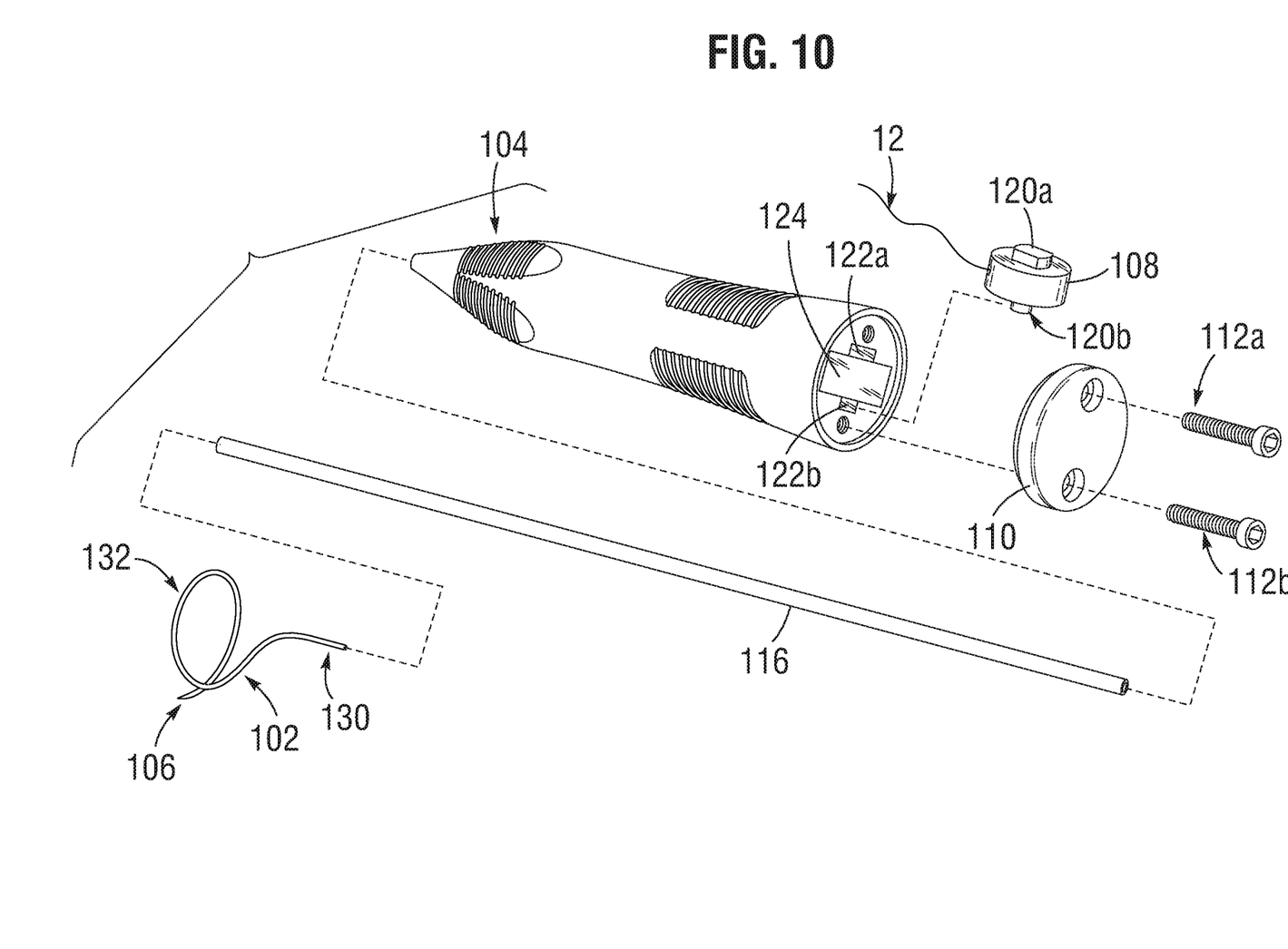

Considering alternative embodiments of devices according to the present invention, FIGS. 8-10 illustrate an alternative embodiment having a handle 100 rather than finger holders as in the embodiment of FIG. 1. In surgery, the surgeon grips the handle 100 and rotates the hand to, in turn, rotate the curved needle 102. The handle may include a thumb placement area 104, preferably aligned with the tip 106 of the needle 102 on the distal end of the device. A suture spool 108 (FIGS. 9 and 10) carrying suture supply 12' is housed within the handle. The cap 110 in this embodiment covers the proximal end of the device. The cap 110 may be secured by a number of means known in the art, such as screws 112a and 112b, clips or other means.

Suture 12 extends from an exit hole of the spool 108, through the shaft 114 of tube 116 that extends from the handle portion. The tube 116 need not necessarily extend directly up to the spool 108, but may optionally extend distally from a cavity 118 in the handle, as in the example of FIG. 9. Generally, the spool is structured so that a pin and key are inserted into a guide cavity in the opening of the handle to keep the spool in alignment with the smaller-diameter tube 116 that may be press-fitted or otherwise secured to a larger tube 118.

While the spool 108 may be any of a variety of different spool types, the spool of FIGS. 8 and 9 includes axis members 120a and 120b extending from either side of a central rotational spool 108. The interior of the handle 100 includes receptors 122a and 122b to receive the axis members 120a and 120b and to permit rotation of the spool 108, and an opening 124 to receive the spool 108. Alternatively, the spool may have a post extending through the spool, protruding out from the spool on either side and about which the spool rotates. The interior of the handle also includes threaded receptors 126a and 126b (FIG. 10) to receive screws or bolts 112a and 112b. The portion of the handle interior that receives the spool and screws or bolts may be a spool housing in the proximal portion of the handle, although the spool housing may be elsewhere in the handle.

Considering the needle 102 in more detail, and referring to FIG. 10, one embodiment of suitable needle has a tip 106 having an opening through which suture 12 extends and exits the tip (FIG. 8). The needle may optionally include a portion 130 that is axially aligned with the longitudinal axis of the handle 100. The needle also includes a helical loop portion 132. In another embodiment, the portion 132 may be approximately a semi-circle, as in FIGS. 3a and 3b, or other suitable configuration that facilitates piercing and threading tissue as, for example, in FIGS. 4-7.

Figures 11, 12:
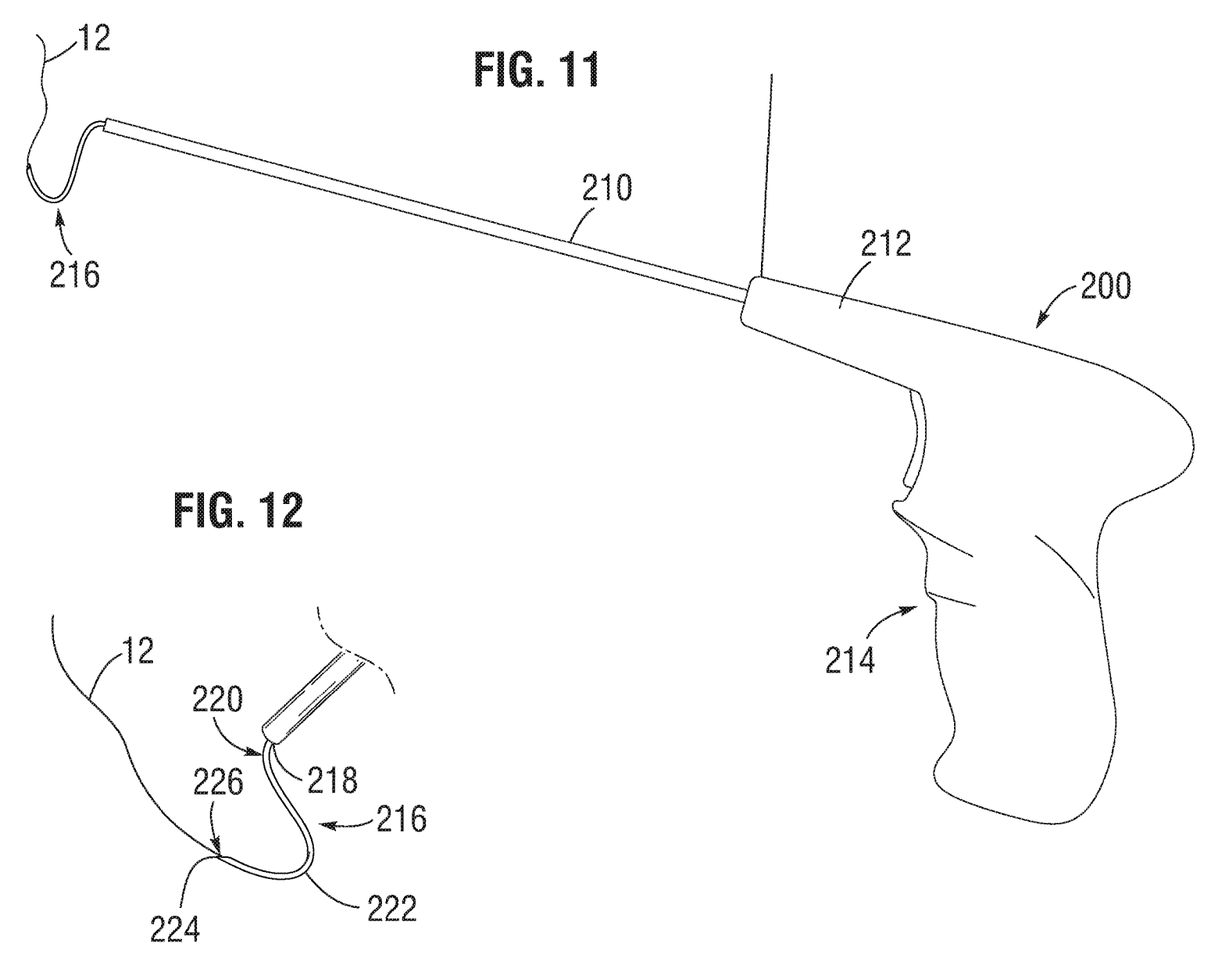
FIGS. 11-13 illustrate a further embodiment of a device according to the present invention.
Figure 13:
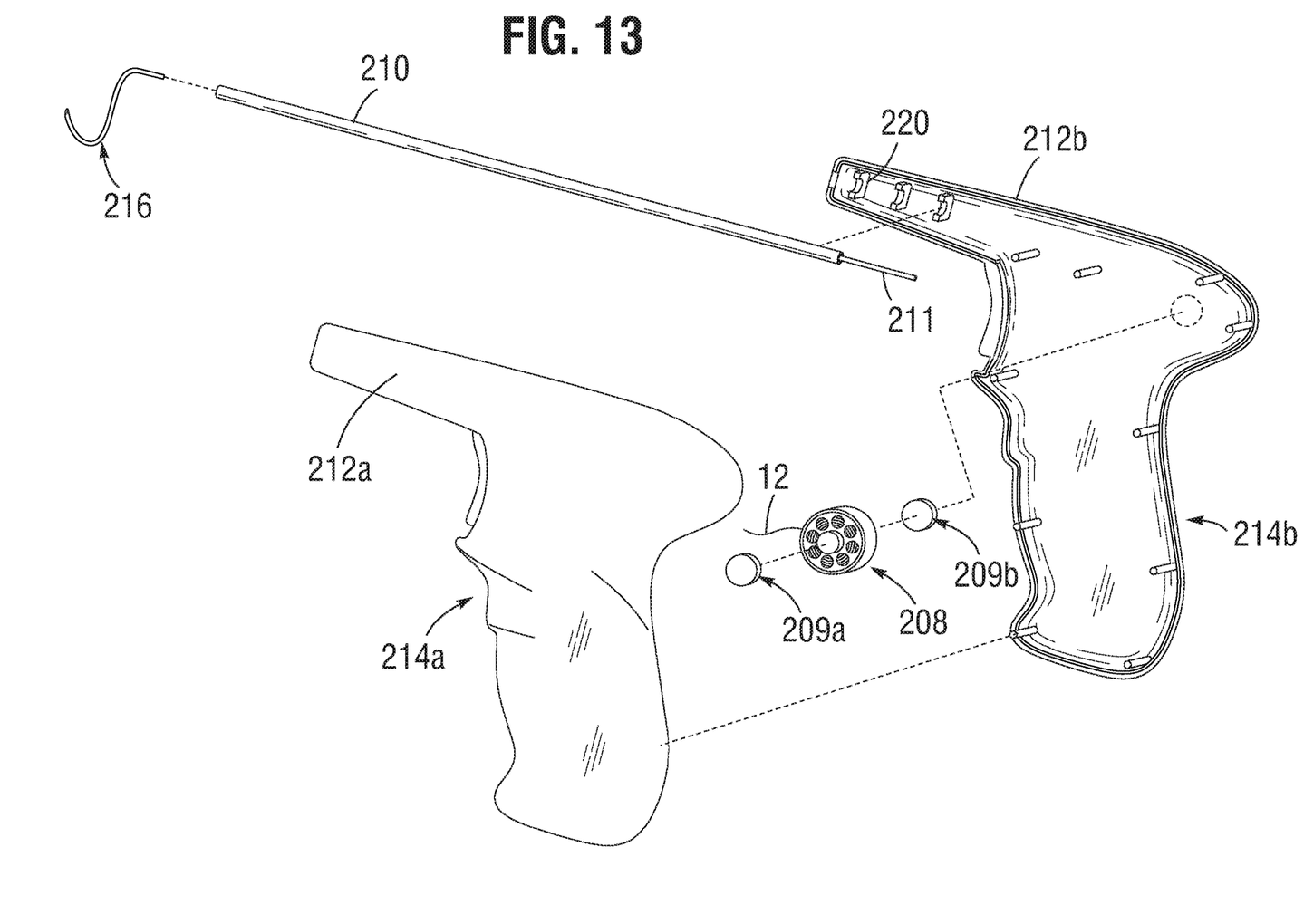

FIGS. 11-13 illustrate a further alternative embodiment having an ergonomic handle 200 having a pistol-like grip. The handle 200 includes a spool 208 (FIG. 13) rotatably mounted within the handle and that feeds suture into the shaft of a tube 210 extending from the handle as in previous embodiments. The handle includes a tube-holding section 212 that extends in the same axial direction as the tube 210. The handle further includes a grip handle 214 extending at an approximately 90 degree angle relative to the tube-holding portion 212. The grip handle 214 is adapted to be gripped and manipulated with the hand, to perform a suturing method such as that illustrated in FIGS. 4-7. A suture-dispensing needle 216 extends from a distal end of the tube 210.

As illustrated in FIG. 13, the handle 200 may be formed from two halves that are secured together by adhesive, heat welding or other methods known in the art. The tube 210 may be supported by brackets 220 on each half of the handle. In the specific embodiment of FIG. 13, an intermediate tube 211 is press-fit into tube 210. Spool 208 is supported and kept in place within the handle by spacers 209a, b when the two halves of the handle 200 are secured together. The spacers 209a, b may be made of rubber, a polymer, or other suitable material. In FIG. 13, sections such as 212, 214 are represented by corresponding complementary portions, such as 212a,b and 214a,b, etc.

The needle 216 may have any of a variety of suitable configurations. In the specific embodiment of FIGS. 11-13, the needle has a portion 218 that extends from tube 210 and that is generally co-axial with the tube 210. The needle has a bend 220 leading to a generally semi-circular portion with a beveled needle tip 222. The needle tip 224 has an opening 226 through which a free end of suture 12 may extend.

Considering details that may optionally be included in specific embodiments, the handle may be made from any of a variety of materials including, without limitation, molded plastic. The tubes may be, for example, hypotubes. One specific, non-limiting example of a suitable hypotube has a 3.2 mm outer diameter, with a 0.075 mm inner diameter. The needle may be integral to the tube. Alternatively, the needle may be attached to the tube by any of a variety of means, such as adhesive, welding, mechanical inter-fitting, or other securing methods known in the art. Similarly, the tube may be integral to the handle, or may be attached to the handle by a variety of securing means known in the art. The needle may include reinforcement, such as with a reinforcing sheath that extends fully or part-way around the needle. The free ends of the suture may be secured together with knots, or with other securing means such as clips.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

What is claimed is:

1. A device for closing an aorotomy during heart valve surgery, comprising: a handle comprising a proximal end, a distal end, and an interior space; the interior space comprising a housing and a spindle rotatably mounted within the housing, a supply of suture supplied on the spindle; the spindle comprising a rotational spool with a first axis member and a second axis member extending outwardly from either side of the rotational spool, the first axis member and the second axis member having different shapes, and an interior of the housing having receptors to receive the first axis member and the second axis member and adapted to permit rotation of the spool; a removable cap that is adapted to be secured to the housing; a tube having a lumen, the tube extending from a distal end of the handle; a curved needle having a lumen, the needle extending from a distal end of the tube and adapted to pierce the aorta, with suture extending from the housing, through the lumen of the tube and the lumen of the needle, and extending out of an opening in the needle; wherein the tube and needle are hypotubes.

2. A device as defined in claim 1, wherein the handle comprises first and second finger holders for manipulating the needle.

3. A device as defined in claim 2, wherein the first and second finger holders are rings spaced distally from the housing.

4. A device as defined in claim 1, wherein the handle is a pistol grip.

5. A device as defined in claim 1, wherein the handle includes a generally tubular portion for gripping with a hand.

6. A device as defined in claim 5, wherein the handle includes a thumb placement area.

7. A device as defined in claim 6, wherein the thumb placement area is aligned with a tip of the needle.

8. A device as defined in claim 1, wherein the needle is helical.

9. A device as defined in claim 1, wherein the needle is semicircular.

10. A device as defined in claim 1, wherein the needle has a beveled tip.

11. A device as defined in claim 1, wherein the needle is integral with the tube.

12. A device as defined in claim 1, wherein the needle is reinforced with a reinforcing sheath that extends around at least a portion of the needle.

13. A device as claimed in claim 1, wherein the first axis member is a locking key.

14. A device for closing an incision in an artery, comprising: a handle comprising a proximal end, a distal end, and an interior space; a housing within the interior space of the handle, a spindle rotatably mounted within the housing, and a supply of suture supplied on the spindle; the spindle comprising a rotational spool with a first axis member and a second axis member extending outwardly from either side of the rotational spool, the first axis member having a non-circular shape, and an interior of the housing having receptors to receive the first axis member and the second axis member and adapted to permit rotation of the spool; a removable cap over the housing; a tube having a lumen, the tube extending from the distal end of the handle; the tube comprising a curved needle at a distal end of the tube, the needle having a lumen, the needle being adapted to pierce the artery; and the suture extending from the housing, through the lumens of the tube and the needle, and extending out of a distal opening at a distal end of the needle; wherein the needle is beveled and is integral with the tube; and the tube has a proximal end with an opening through which the suture enters the tube, the proximal end of the tube being spaced a distance from the housing.

15. A device as defined in claim 14, wherein the needle includes a distal portion that extends in the direction of a longitudinal axis of the handle, and a proximal curved portion.

16. A device as defined in claim 15, wherein the curved portion of the needle comprises one of a semi-circular needle and a helical needle.

17. A device as defined in claim 14 wherein the needle is a hypotube.

18. A device as defined in claim 14 wherein both the needle and the tube are hypotubes.

19. A device as defined in claim 14, wherein the needle is reinforced with a reinforcing sheath that extends around at least a portion of the needle.

20. A device as defined in claim 14, wherein the tube is a second tube, a first tube extending distally from the housing through at least a portion of the handle, the second tube being secured within a distal portion of the first tube, such that a proximal end of the second tube is spaced a distance from the housing.

21. A device as claimed in claim 14, wherein the first axis member is a locking key.

* * * * *